United States Patent [19]

Kawahara

[11] Patent Number: 5,672,693
[45] Date of Patent: Sep. 30, 1997

[54] GLYCOSPHINGOLIPIDS

[75] Inventor: Kazuyoshi Kawahara, Tokyo, Japan

[73] Assignees: Kabushikikaisha Kibun Shokuhin; The Kitasato Institute, both of Tokyo, Japan

[21] Appl. No.: 451,729

[22] Filed: May 26, 1995

Related U.S. Application Data

[63] Continuation of Ser. No. 245,837, May 19, 1994, abandoned, which is a continuation of Ser. No. 90,104, filed as PCT/JP92/00055 Jan. 23, 1992, abandoned.

[30] Foreign Application Priority Data

Jan. 23, 1991 [JP] Japan ................................ 3-006344

[51] Int. Cl.$^6$ ............................................. C07H 15/04
[52] U.S. Cl. .......................... 536/17.9; 536/17.2; 435/74; 514/25
[58] Field of Search ..................... 536/17.2, 17.9; 435/74; 514/25

[56] References Cited

FOREIGN PATENT DOCUMENTS 0255717 2/1988 European Pat. Off. .

OTHER PUBLICATIONS

Akihiro Yamamoto, "Sphingoglycolipid and its metabolism in gram–negative aerobic bacteria" pp. 201–219. Osaka–Shiritsu Daigaku Igaku Zasshi, vol. 31, No. 2 (1982) Month Not Available.

K. Kawahara et al. "Chemical structure of glycosphingolipids isolated from *Sphingomonas paucimobilis*" pp. 107–110. FEBS Letters, vol. 292, No. 1–2 (1991) Month Not Available.

*Primary Examiner*—Kathleen K. Fonda
*Attorney, Agent, or Firm*—Nixon & Vanderhye P.C.

[57] ABSTRACT

Glycosphingolipid compounds represented by the following formula

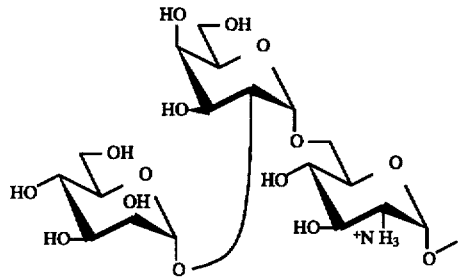

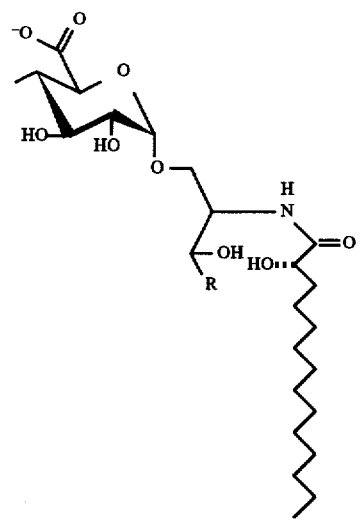

wherein R is

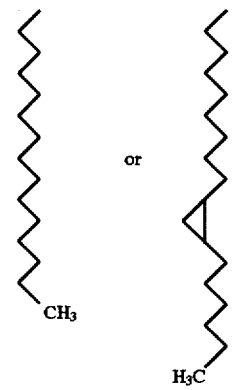

possess B cell mitogen activity and can be used as B cell activators.

2 Claims, 10 Drawing Sheets

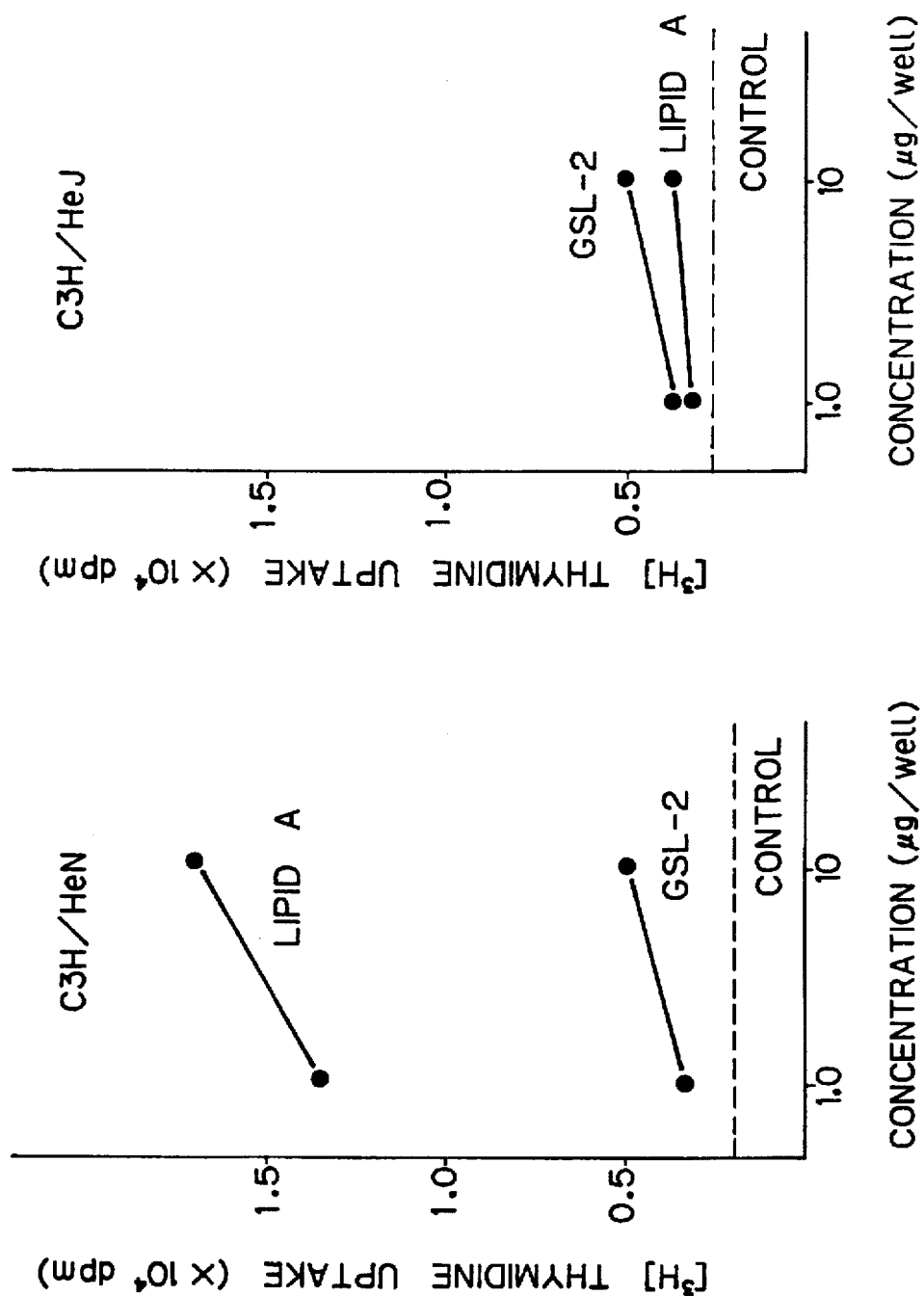

GLYCOSPHINGOLIPIDS

This is a continuation of application Ser. No. 08/245,837, filed May 19, 1994, now abandoned, which is a continuation of application Ser. No. 08/090,104 filed Jul. 20, 1993 now abandoned, which is a 371 of PCT/JP92/00055 filed Jan. 23, 1992.

TECHNICAL FIELD

The present invention relates to a novel glycosphingolipid having an immune-activating activity.

TECHNICAL BACKGROUND

Glycosphingolipids are substances present in the outer layers of animal cells, etc. and are considered to have a role to play in recognition mechanism.

On the other hand, Gram negative bacteria have an outer membrane composed of lipopolysaccharides, proteins and phosphoric acid in the cell surface layer thereof, and perform an exchange operation between the inside and outside of a cell through the membrane. Accordingly, lipopolysaccharides are present commonly in all Gram negative bacteria and are considered to be a substance essential to the bacteria. However, it has been found that a bacterium known as *Pseudomonas paucimobilis* which is an aerobic Gram negative bacterium and which is one of the opportunistic infectious bacteria contains no 3-hydroxy aliphatic acid which is known as a main fatty acid component of lipopolysaccharides. Recently, it has been proposed that the above bacterium be designated as Genus Sphingomonas since the bacterium contains a glycosphingolipid as a microbial cell lipid and, in addition, many other taxonomical characteristics of the bacterium are different from those of the typical bacteria of the Genus Pseudomonas. *Sphingomonas paucimobilis* is expected to contain quite specific lipopolysaccharides.

TECHNICAL PROBLEMS

An object of the present invention is to obtain a novel glycosphingolipid having a useful biological activity by isolating a glycolipid from the above-described bacteria, and analyzing its chemical structure and studying biological activities thereof.

MEANS FOR SOLUTION

The present inventors have succeeded in isolating and identifying the object novel glycosphingolipid by using an appropriate combination of treatment steps such as extraction of the cell membrane of the bacteria of the Genus Sphingomonas with organic solvents, and column chromatography and the like.

BRIEF DESCRIPTION OF THE DRAWINGS

FIG. 10 is a graph showing differences in the functional mechanism of GSL-2 and endotoxin (Lipid A).

DETAILED DESCRIPTION OF THE INVENTION

*Sphingomonas paucimobilis*, *Sphingomonas capsulata* or *Sphingomonas adhaesiva* is cultured in an appropriate culture medium to obtain a large quantity of microbial cells which are then freeze-dried. Then, the dried microbial cells are extracted successively with acetone and subsequently chloroform/methanol (2:1, v/v) to fractionate them into a solvent fraction and a cell residue. Following this, each of the cell residues is extracted with chloroform/methanol (1:3, v/v) and the resulting crude extract is analyzed by thin layer chromatography to isolate desired types of the glycosphingolipid (refer to FIG. 1). This crude extract fraction is purified by silica gel chromatography, then eluted with mixed solvents each having different mixing ratios of chloroform/methanol (2:1), (1:1) and (1:3), and subjected to thin layer chromatography to obtain the desired purified lipid.

Figure 2:
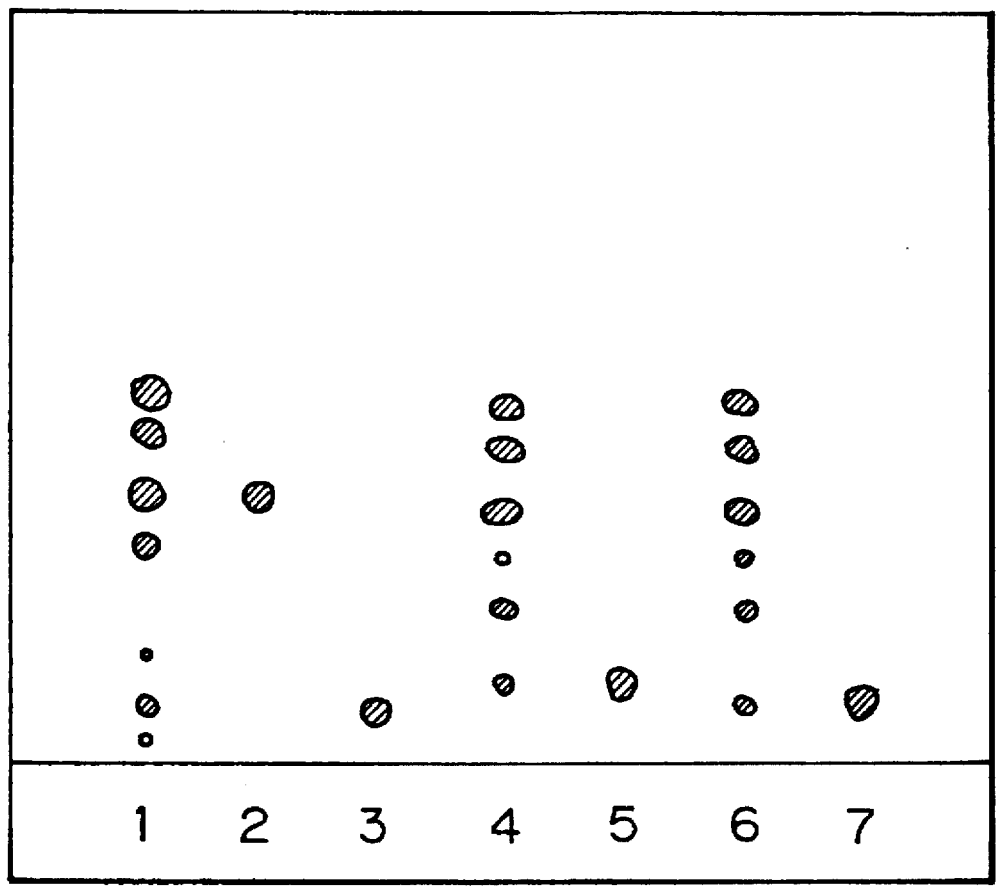
FIG. 2 is a graph showing the results of analysis by thin layer chromatography of a microbial cell lipid of each of the freeze-dried microbial cells and purified GSL.

Each of the resulting purified glycolipids was confirmed by thin layer chromatography to be a single substance (refer to FIG. 2). Further, novel glycosphingolipids represented by the following formulae were identified upon analysis of their chemical structures by the method described below.

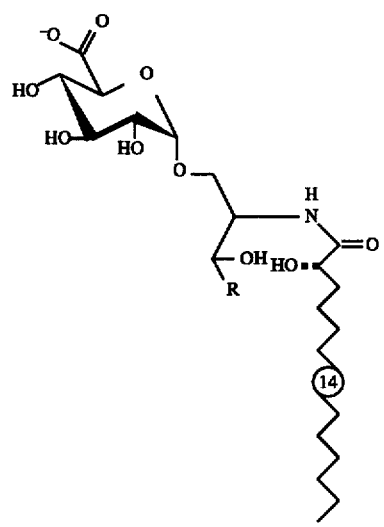
GSL-1
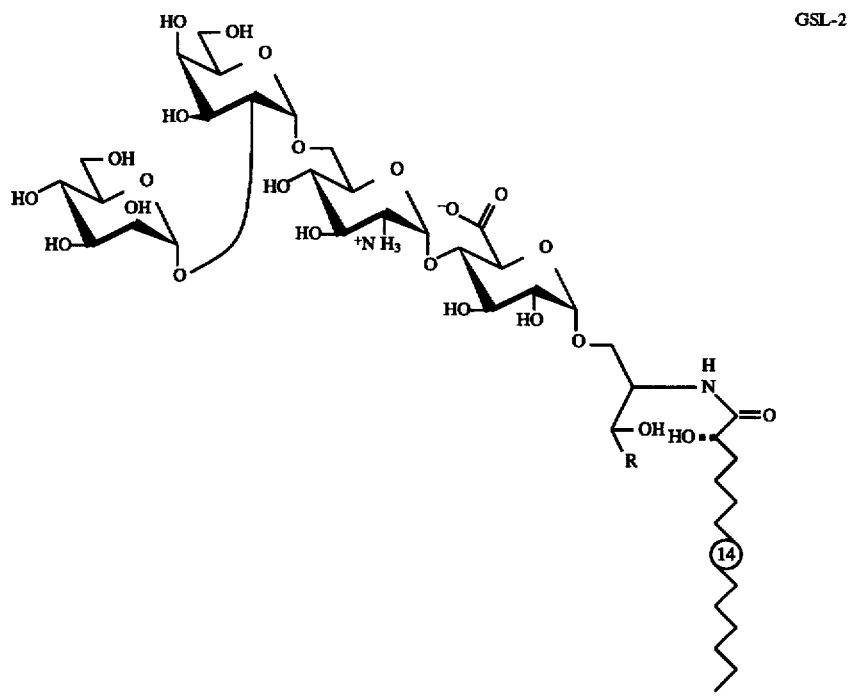
GSL-2

GSL-3
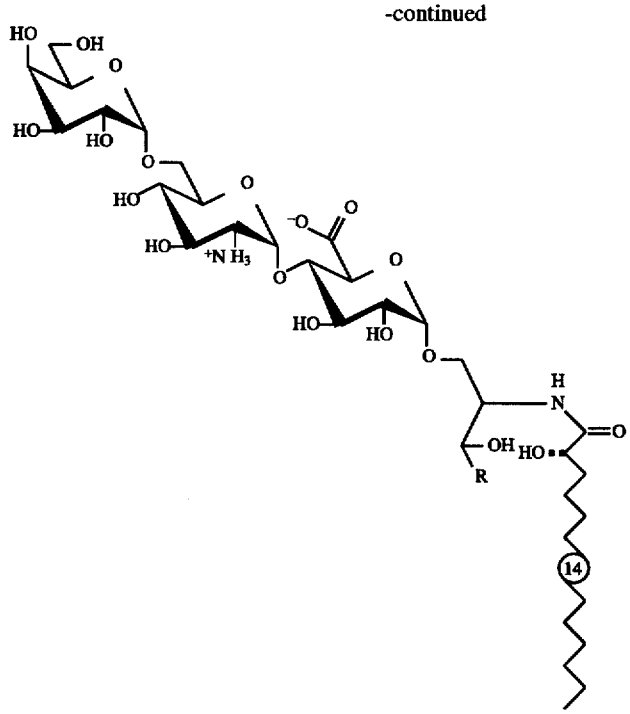
GSL-4
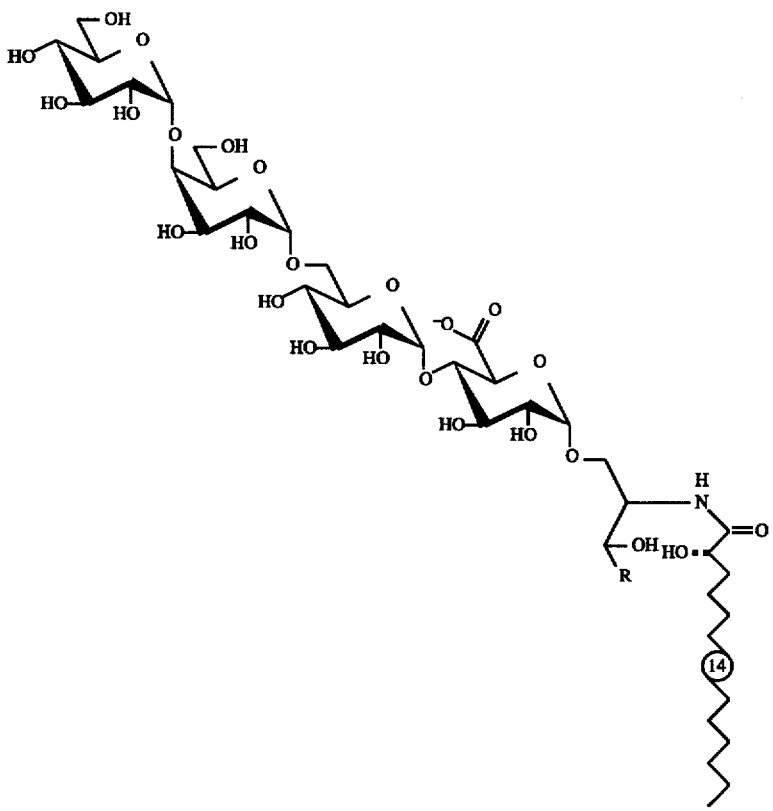
wherein R is selected from the following hydrocarbons (provided that R is not a hydrocarbon of $C_{18}$ in the case of GSL-1):

R = 

R = 

R = 

The glycolipid obtained in accordance with the present invention does not exhibit an endotoxin activity which is known to be inherent in the lipopolysaccharide as one of the glycolipids originating from known Gram negative bacteria. On the other hand, the glycolipid of the present invention possesses a B cell mitogen activity, but the above activity was found to be different from that of the conventional lipopolysaccharide which exhibits an activity in lipopolysaccharide-nonresponsive mice.

Thus, the object compound of the present invention exhibits a B cell activating effect and a differentiation-deriving effect on animal cells, and is expected to be useful as an immunoactivator.

The present invention is further described in more detail with reference to Example.

EXAMPLE

1. Cultivation of Strains Used

Each of the following strains was used:

Sphingomonas paucimobilis KK0001 (Deposit No. 3631 at the Fermentation Research Institute under the Budapest treaty: FERM BP-3631 (transferred from Deposit No. 11820 at the Fermentation Research Institute: FERM P-11820))

Sphingomonas pancimobilis, KK0002 (Deposit No. 3632 at the Fermentation Research Institute under the Budapest treaty: FERM BP-3632 (transferred from Deposit No. 11821 at the Fermentation Research Institute: FERM P-11821))

Sphingomonas pancimobilis, KK0003 (Deposit No. 3633 at the Fermentation Research Institute under the Budapest treaty: FERM BP-3633 (transferred from Deposit No. 11822 at the Fermentation Research Institute: FERM P-11822))

Sphingomonas pancimobilis, KK0004 (Deposit No. 3634 at the Fermentation Research Institute under the Budapest treaty: FERM BP-3634 (transferred from Deposit No. 11823 at the Fermentation Research Institute: FERM P-11823))

Sphingomonas capsulata KK0005 (Deposit No. 3709 at the Fermentation Research Institute: FERM BP-3709)

Sphingomonas adhaesiva KK0006 (Deposit No. 3710 at the Fermentation Research Institute: FERM BP-3710)

Each of the strains was cultivated using a culture medium containing 1% glucose, 0.5% yeast extract, 0.5% casamino acid, 0.2% $(NH_4)_2SO_4$, 0.2% $K_2HPO_4$ and 0.1% $MgSO_4 \cdot 7H_2O$ in a jar fermentor at 30° C. for 24 hours. The resulting culture liquid was centrifuged to recover microbial cells and the cells were freeze-dried.

2. Extraction and Purification

The freeze-dried microbial cells were extracted with acetone and then chloroform/methanol (C/M) (2:1, v/v) to fractionate the microbial cells into a solvent fraction and a microbial cell residue. Then, the microbial cell residue was extracted with C/M (1:3, v/v) at a temperature of 80° C. for 1 hour to obtain a crude extract fraction. The resulting fraction was purified by silica gel (Silica Gel 60, Merck & Co., 70 to 230 mesh) column chromatography. For the elution, C/M (2:1, v/v), C/M (1:1, v/v) and C/M (1:3, v/v) were used, and a purified lipid was recovered from the C/M (1:3, v/v) eluate fraction.

3. Analysis and Identification of Chemical Composition

1) TLC Analysis

The crude extract fraction obtained during the above-described purification process and the purified glycolipid obtained by silica gel column chromatography were analyzed by thin layer chromatography (TLC) using a silica gel 60 aluminum plate (Merck & Co.). As a developing solution, chloroform/methanol/acetic acid/water (25:15:4:2) was used.

Figure 1:
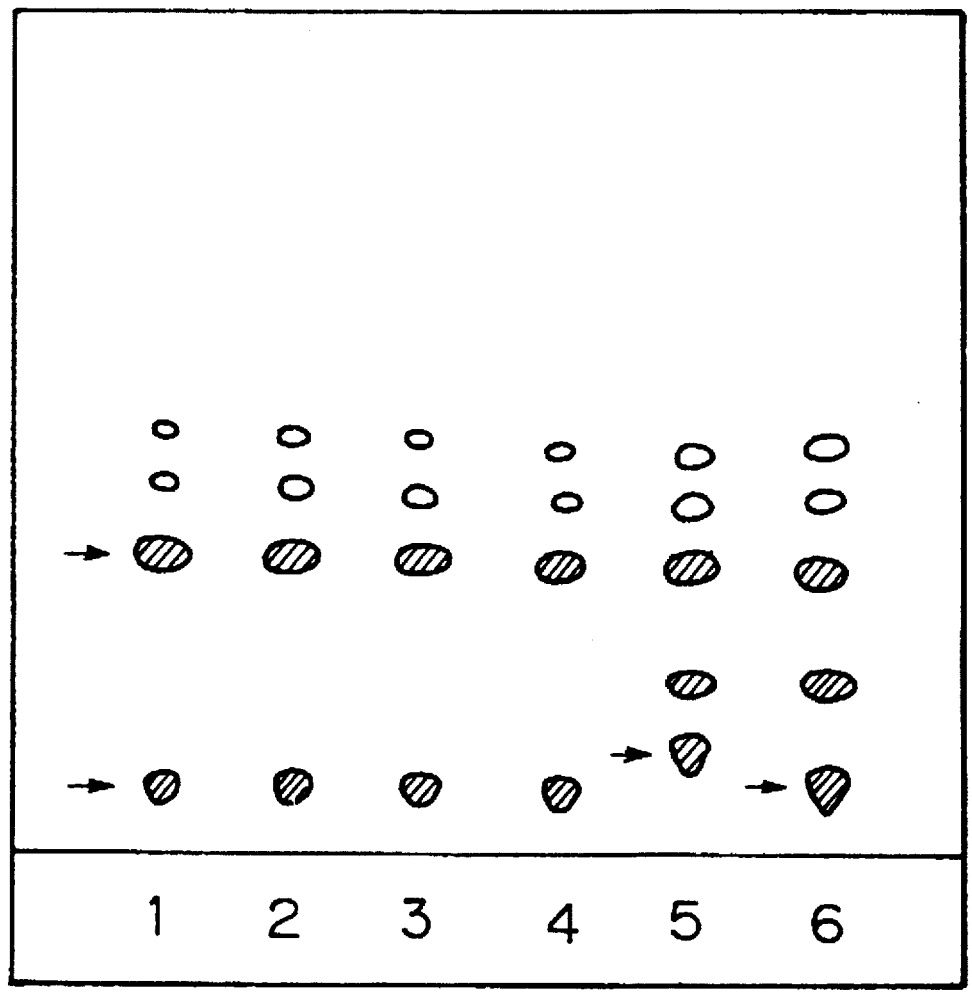
FIG. 1 is a graph showing the results obtained by extracting each of the freeze-dried microbial cells obtained in Example with chloroform/methanol (C/M) (2:1, v/v), extracting the residue of the microbial cells with C/M (1:3, v/v), and analyzing the C/M (1:3, v/v) extract fraction by thin layer chromatography.

The results of analysis of the above-described extract fraction (C/M=1:3, v/v) are shown in FIG. 1. Lanes 1 to 4 show the spots obtained by the above-described TLC analysis of the extract fractions of S. paucimobilis KK0001 to KK0004 strains origin, respectively, and lanes 5 and 6 show those of S. capsulata KK0005 and S. adhaesiva strains origin, respectively. The spots indicated by an arrow mark (upper) in lane 1, an arrow mark (lower) in lane 1, an arrow mark in lane 5 and an arrow mark in lane 6 stand for GSL-1, GSL-2, GSL-3 and GSL-4, respectively.

FIG. 2 shows the results of the TLC analysis of microbial cell lipid and purified GSL of each of the strains. Lane 1 shows the results of analysis of the microbial cell lipid of S. paucimobilis KK0001 (a combined fraction of the C/M (2:1) extract fraction and the C/M (1:3) extract fraction), and lanes 2 and 3 show the results of analysis of purified GSL-1 and GSL-2, respectively. Lanes 4, 5, 6 and 7 show the results obtained from the samples of microbial cell lipid of S.

*capsulata* KK0005, purified GSL-3, microbial cell lipid of *S. adhaesiva* KK0006 and purified GSL-4, respectively.

It is apparent from the results of the TLC analysis shown in FIG. 2 that in the crude extract fractions obtained from each of the cultured strain, GSL-1 and GSL-2 are contained in the microbial cell lipid of *S. paucimobilis*; GSL-3 and GSL-1 are contained in the microbial cell lipid of *S. capsulata*; and GSL-4 and GSL-1 are contained in the microbial cell lipid of *S. adhaesiva*.

2) Analysis of Chemical Composition

Analysis of aliphatic acid moieties was conducted by gas chromatography (GLC) after hydrolysis with 4N HCl at 100° C. for 5 hours and then methyl esterification. Neutral sugars were analyzed by GLC after hydrolysis with 0.1N HCl at 100° C. for 48 hours and then conversion into an acetylalditol derivative. As a column of GLC, CBP-1 (produced by Shimazu Seisakusho, 25 mm. inside diameter of 0.2 mm) was used. Amino sugars were analyzed as a phenylisothiocarbamyl derivative using high performance liquid chromatography (HPLC). The HPLC analysis was performed using an ODS column. The carbazole sulfuric acid method was used for the quantitative determination of uronic acid.

The results are shown in Table 1.

TABLE 1

Chemical Composition of Purified Glycolipids

| Component | μmol/mg | | |
|---|---|---|---|
| | GSL-2 | GSL-3 | GSL-4 |
| 2-Hydroxymyristic acid (a) | 0.74 | 1.15 | 0.55 |
| Glucosamine (b) | 0.60 | 0.37 | — |
| Mannose (c) | 0.64 | 0.69 | 0.46 |
| Galactose (c) | 0.53 | — | 0.78 |
| Uronic acid (d) | 0.38 | 0.30 | 0.46 |

Note:
a: All the acids were in base-stable forms; that is, amido bond forms.
b: Glucosamine was measured by the Morgan-Elson method and identified by HPLC and GLC. It was assumed that the total amount of glucosamine of GSL-2 and GSL-3 could not be detected.
c: Measured by GLC as an acetylalditol derivative.
d: It was assumed that the total amount of uronic acid could not be detected. Insufficient detection of glucosamine and uronic acid of GSL-2 and GSL-3 was due to a GlcN—GlcA bond which is stable against acid hydrolysis.

3) Identification of Disaccharide Released by Decomposition with Strong Acid

The purified glycolipid was hydrolyzed with 4N HCl at 100° C. for 5 hours, and the hydrolyzate was analyzed by high-voltage paper electrophoresis (HVPE). HVPE was conducted using a buffer solution of pyridine/acetic acid/water/formic acid (1:10:90:about 3, v/v)(pH 2.8) under the conditions of 1,500 V for 2.5 hours.

Figure 3:
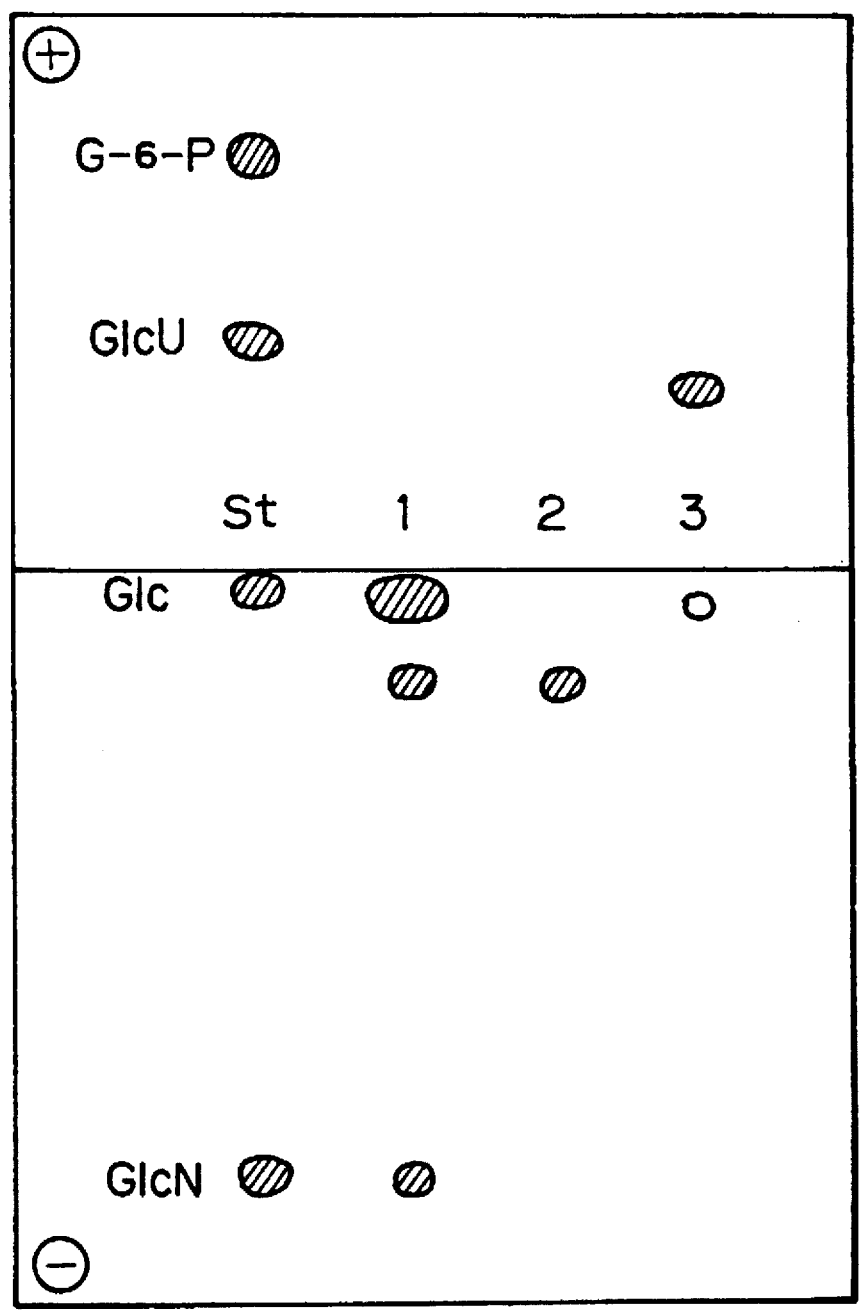
FIG. 3 is a graph showing the results of high-voltage paper electrophoretic analysis using a 4N HCl hydrolyzate of purified glycolipid (GSL-2)

The results regarding the sample of GSL-2 are shown in FIG. 3. The results of analysis of the above-described hydrolyzate are shown in lane 1. Of three spots in lane 1, a substance contained in the intermediate spot was extracted from the filter paper and again analyzed by HVPE which is shown in lane 2. Further, this unknown substance was N-acetylated and then analyzed by HVPE to obtain the spot shown in lane 3.

As a result of the HVPE analysis and the ninhydrin-positive reaction of this substance, this unknown substance was found to have an amino group and a carboxyl group.

Figure 4:
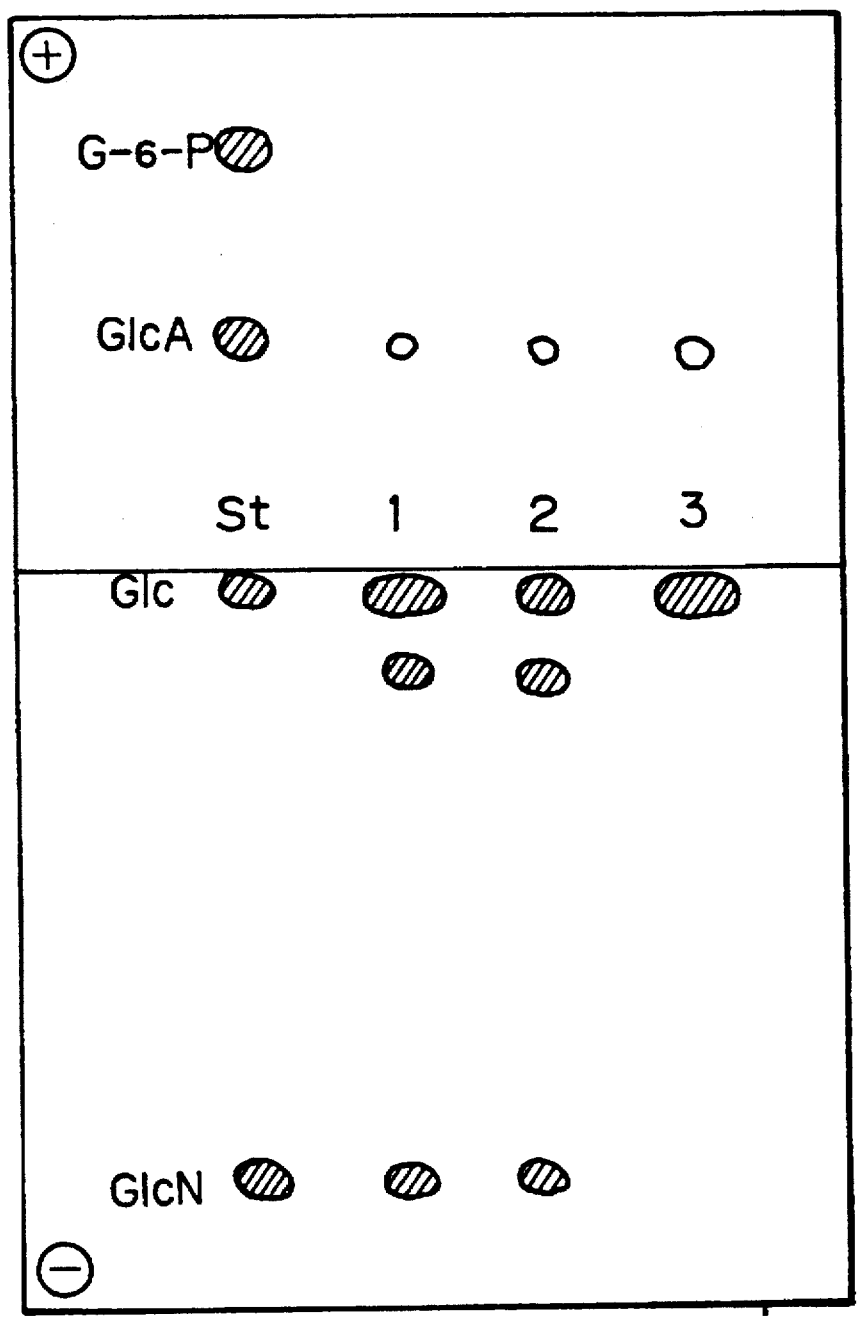
FIG. 4 is a graph showing the results of high-voltage paper electrophoretic analysis using a 4N HCl hydrolyzate of each of purified glycolipids (GSL-2, -3 and -4)

FIG. 4 shows the results obtained by the electrophoresis (HVPE) under the same conditions as used in GSL-2 of FIG. 3 but using GSL-2, GSL-3 and GSL-4 as samples. Standard, GSL-2, GSL-3 and GSL-4 were used in lane St, lane 1, lane 2 and lane 3, respectively.

Figure 5:
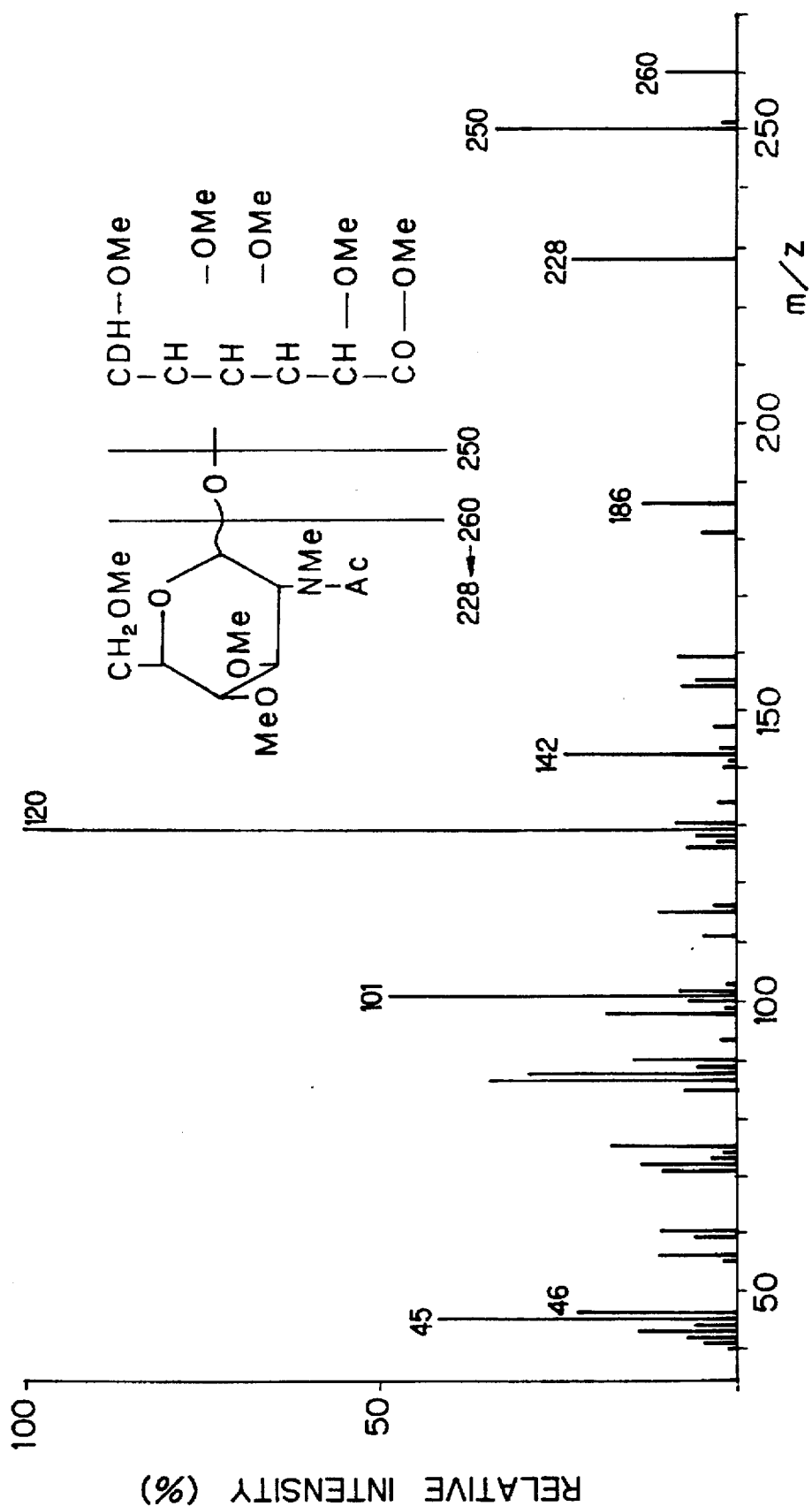
FIG. 5 is a chart obtained from mass spectrographic analysis (electron ionization method) of a completely methylated disaccharide isolated from a 4N HCl hydrolyzate of the purified glycolipids.

After N-acetylating the above-described unknown substance of GSL-2 origin, the substance was then reduced with $NaBD_4$ and completely methylated using an improved method of the Hakomori method. The resulting derivative was found to have a molecular weight of 526 as determined by the mass spectrography (chemical ionization method). Also, when the substance was analyzed by mass spectrography (electron ionization method: EI-MS), it showed a fragment pattern as shown in FIG. 5. It was found from FIG. 5 that the original substance is a disaccharide composed of glucosamine at the non-reducing terminal and uronic acid at the reducing terminal.

Figure 6:
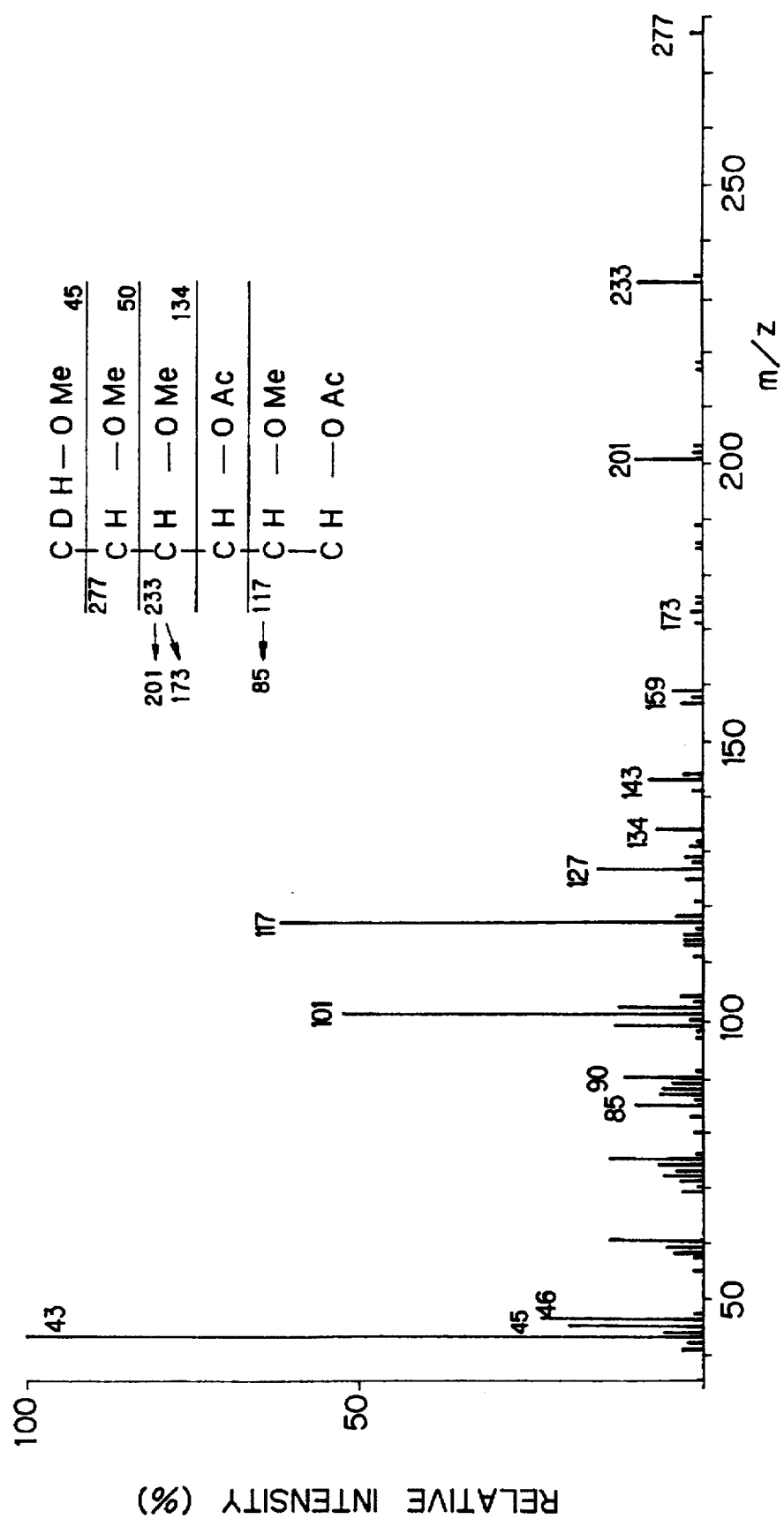
FIG. 6 is a chart obtained from mass spectrographic analysis of uronic acid-origin peaks obtained by reducing the carboxyl group of the completely methylated disaccharide, followed by hydrolysis with trifluoroacetic acid and acetylation.

Then, the carboxyl group of the methylated disaccharide was reduced to a hydroxyl group and, there-after, acetylated by hydrolysis using 2N trifluoroacetic acid (TFA) at 120° C. for 2 hours. The resulting peak of uronic acid origin was analyzed by gas chromatography/mass spectrometry (GC/MS) to obtain FIG. 6. As shown in FIG. 6, the mass spectrometry (GC/MS) indicating 4,6-Ac-1,3,5-Me-hexitol was obtained. On the other hand, when the substance was again methylated after hydrolysis, a completely methylated hexitol was obtained and, as a result of identification by its retention time on GLC, this substance was found to be methylated glucitol. From the above results, the disaccharide in the 4N HCl hydrolyzate of the glycolipid of GSL-2 which is one of the object substances of the present invention was identified as Glc-1,4-GlcUA.

On the other hand, GSL-3 and GSL-4 were hydrolyzed with 4N HCl under the same conditions as in GSL-2, and, after acetylation, the hydrolyzate was reduced with $NaBD_4$, completely methylated and analyzed by Gc-MS.

From the hydrolyzate of GSL-3, completely methylated GlcN-1,4-GlcA-ol, GlcA-ol, GlcN-ol and Gal-ol were detected.

Figure 7:
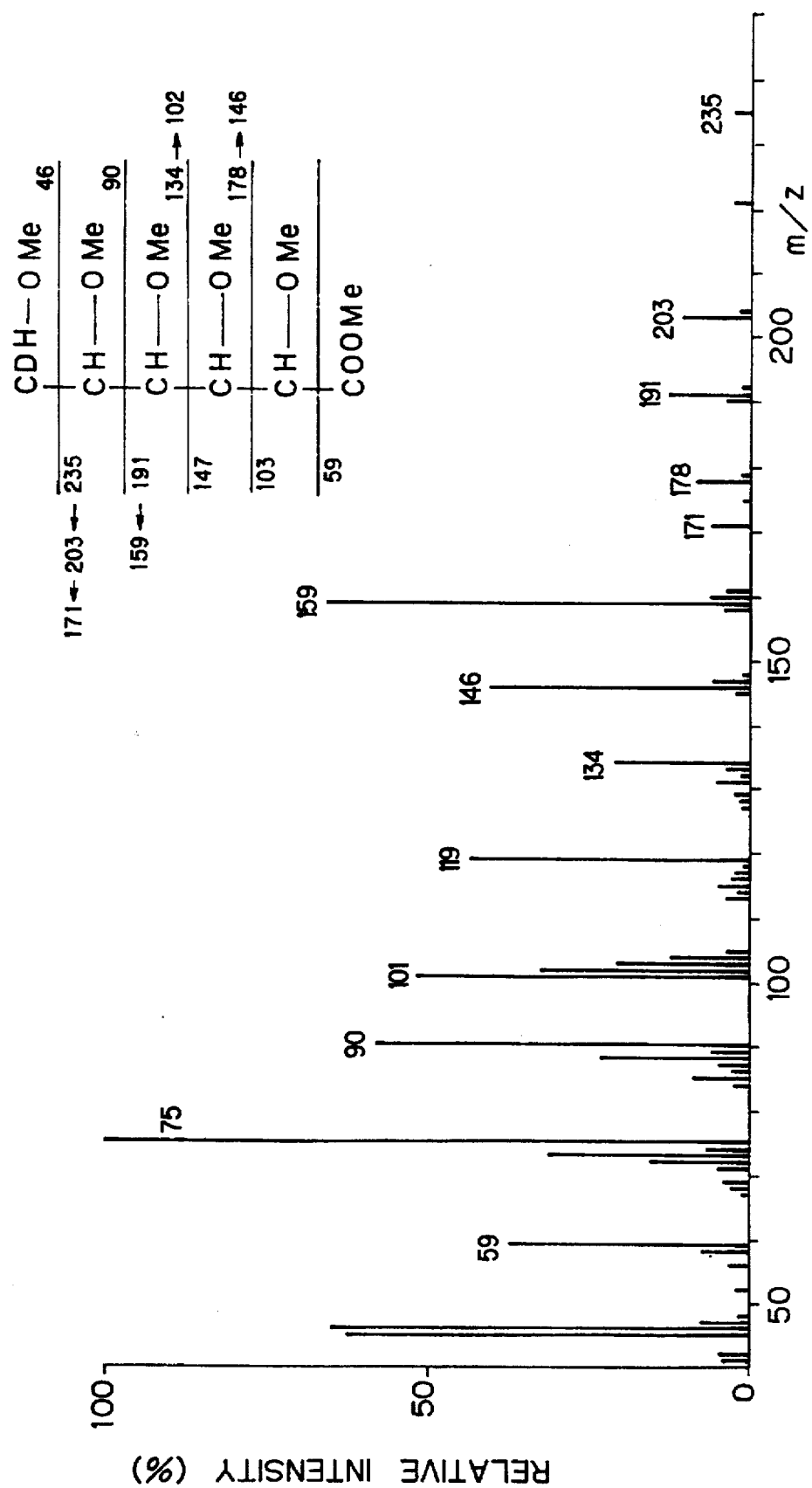
FIG. 7 is a chart showing the results of mass spectrographic analysis on a reduced and methylated derivative of GlcA released from GSL-4.

Similarly, completely methylated GlcA-ol, Gal-ol and Glc-ol were detected from GSL-4. They were confirmed by reducing GlcA released from GSL-4 and analyzing the methylated derivative by EI-MS (refer to FIG. 7).

4) Methylation Analysis of Oligosaccharide

A hydrazine decomposition was performed at 103° C. for 40 hours in order to study the oligosaccharide moiety of glycolipid of the object substance GSL-2, and the resulting oligosaccharide was cetylated, reduced and then completely methylated. After reducing the carboxyl group, the resulting compound was hydrolyzed with 1N TFA at 120° C. for 2 hours, reduced, acetylated and analyzed by GC-MS. As a result, 1,5-Ac-2,3,4,6-Me-mannitol, 1,2,5-Ac-3,4,6-Me-galactitol and 1,5,6-Ac-3,4-Me-2-deoxy-2-(N-Me, Ac)-glucitol were detected. Thus, it was found that, in the original saccharide, mannose is at the non-reducing terminal, galactose is substituted at the 2-position and glucosamine is substituted at the 6-position.

Also, 1,5-Ac-2,3,4,6-Me-galactitol and 1,5,6-Ac-3,4-Me-2-deoxy-2-(N-Me, Ac)-glucitol were detected from the object substance GSL-3. Thus, it was found that, in the original saccharide chain, galactose is at the non-reducing terminal and glucosamine is substituted at the 2-position.

5) NMR Analysis of Purified Glycolipid

The purified glycolipids of GSL-2, GSL-3 and GSL-4 were dissolved in $CDCl_3$/methanol-d4/$D_2O$ (1:3:0.1, v/v) and analyzed by $^1$H-NMR and $^{13}$C-NMR at 360MHz. From the analysis of signals from the aromeric region, it was found that three or four glycoside bonds are all α-bonds. Further, it was considered that a sphingosine residue is present and forms a ceramide with 2-hydroxymyristic acid.

6) Identification of Sphingosine

The purified glycolipid was hydrolyzed with 0.2N HCl/methanol at 65° C. for 5 hours to release sphingosine. After oxidation of sphingosine with $Pb(IV)OAc_4$ and then reduction, the resulting long chain alcohol was converted into a nicotinic acid ester or into a TMS form and analyzed by mass spectrometry (electron ionization method). As a result, it was found that sphingosine contained in the glycolipids of GSL-1 and GSL-2 was mostly a mixture of $C_{18}$-sphinganine and 13,14-cis-methylene-$C_{20}$-sphinganine (mixing ratio, about 1:1), but it also contained a small amount of 13,14-cis-unsaturated-$C_{20}$-sphinganine.

Figure 8:
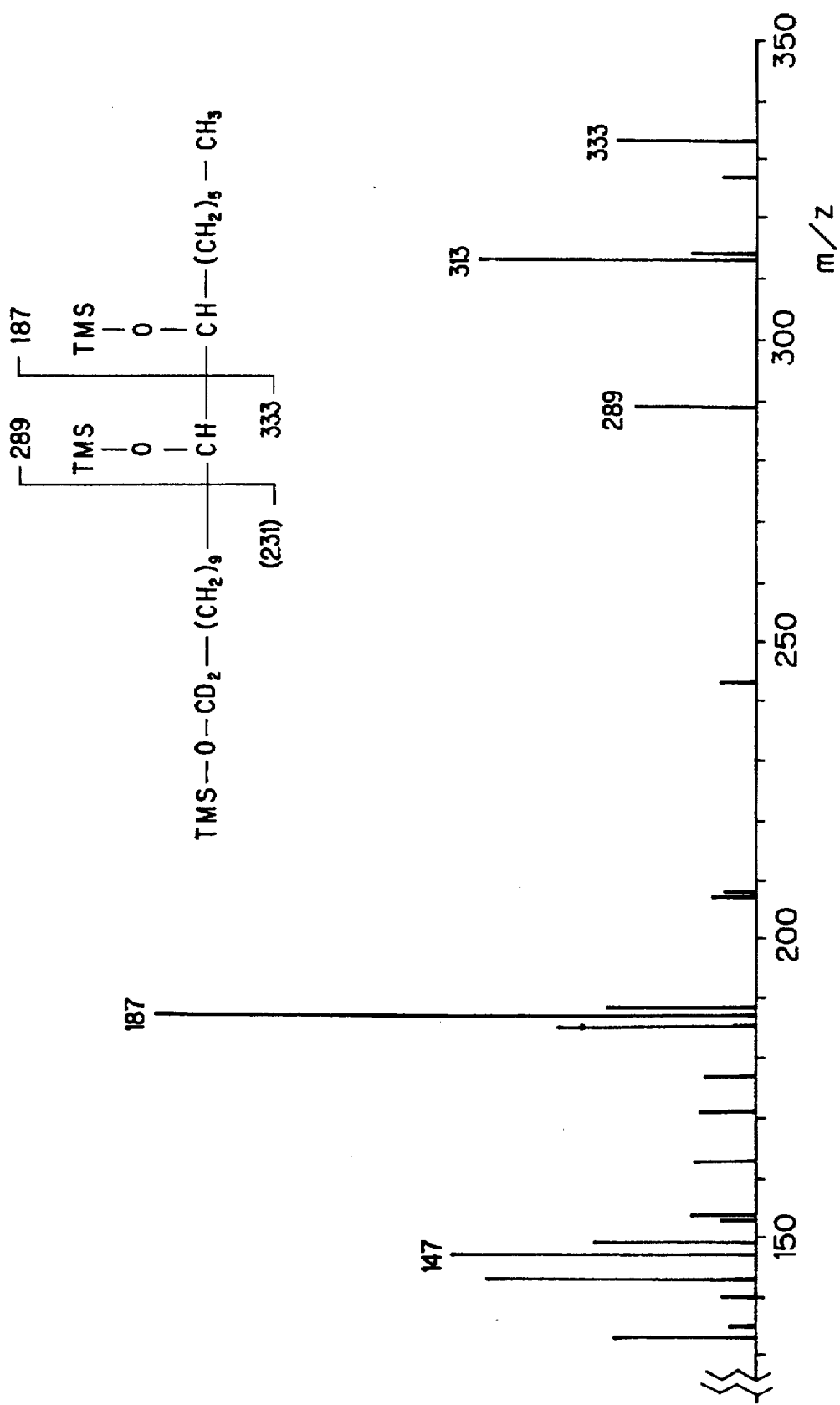
FIG. 8 is a chart showing the results of mass spectrographic analysis on a TMS derivative of a long chain alcohol obtained from sphinganine contained in GSL-3 and GSL-4.

Also, sphingosines released from GSL-3 and GSL-4 were similarly oxidized, reduced, converted into a TMS form and then analyzed by GC-MS. As a result, it was found that a large amount of 13,14-cis-unsaturated-$C_{20}$-sphinganine was contained therein as compared with GSL-1 and GSL-2. (The mixing ratio of $C_{18}$-sphinganine: 13,14-cis-methylene-$C_{20}$-sphinganine: 13,14-cis-unsaturated-$C_{20}$-sphinganine was about 1:2:2) (refer to FIG. 8). Further, GSL-2, GSL-3 and GSL-4 were analyzed by laser-desorption mass spectrography (LD-MS) to determined the total molecular weight and, as a result, the above-described components and the mixing ratio were confirmed.

Experimental Example: Biological Activity Test

1—1. B Cell Mitogen Activity

Spleen cells were prepared from the spleen of mice (C3H/HeN, 7-week old) and spread on a 96-well tissue culture plate in an amount of $5 \times 10^5$ cells/well. Then, each of GSL-1 to GSL-4 was added to the well and cultivated in a $CO_2$ incubator for 2 days. The culture medium used was RPMI Medium (Gibco) added thereto 10% FCS (Gibco).

Then, [$^3$H]thymidine was added to each of the wells at 1 μCi/well, and the cultivation was conducted for 4 hours. After cultivation, cells were recovered on a glass filter, and the radioactivity of the cells was measured by a liquid scintillation counter.

Figure 9:
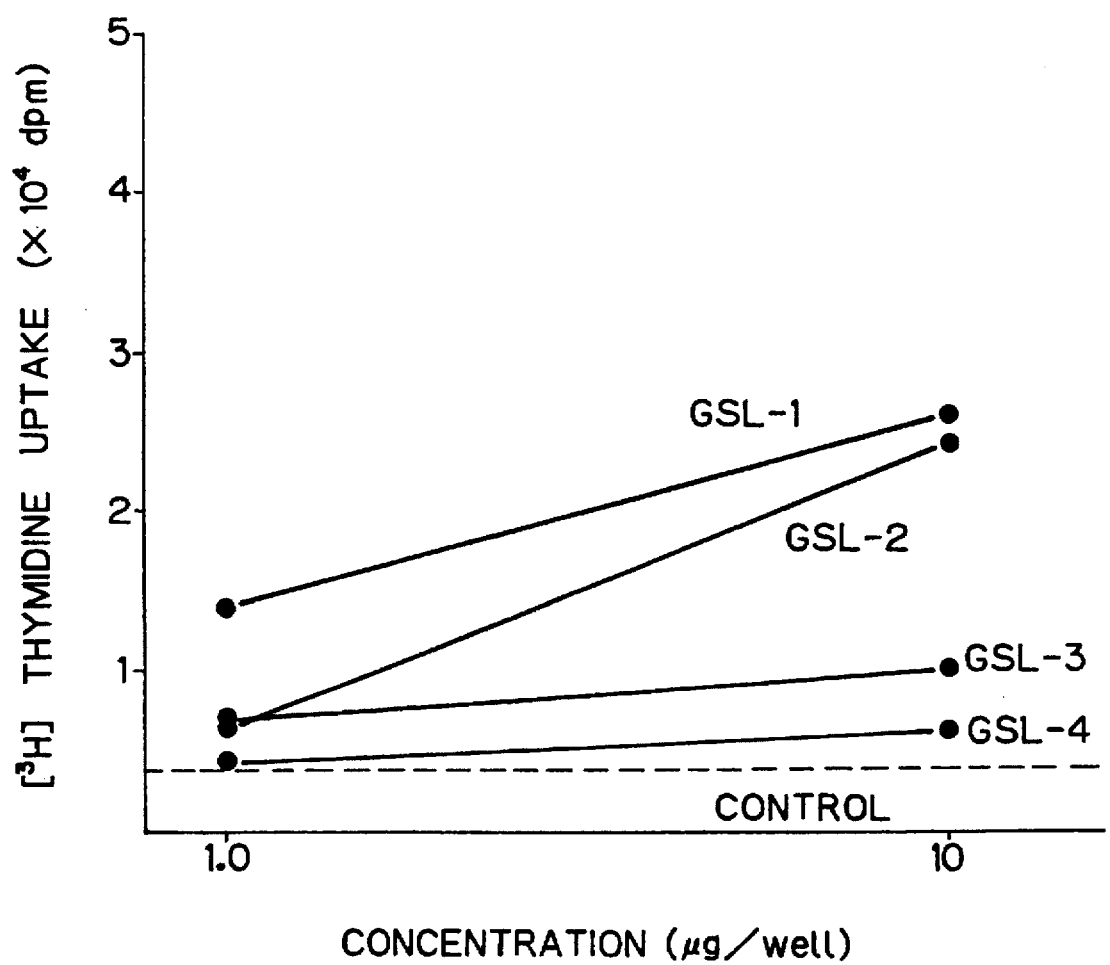
FIG. 9 is a graph showing a B cell mitogen activity of each GSL.

The results are shown in FIG. 9. In each of GSL's, significant uptake of thymidine was observed.

1-2. B Cell Mitogen Activity of GSL-2

GSL-2 which exhibited a high activity in the above 1—1 Test was compared with Lipid A. The test was conducted under the same conditions as described for 1—1 above, and the results are shown in FIG. 10.

Lipid A is an active center of endotoxin (a lipopolysaccharide) and in this test a chemically synthesized product thereof was used. Mice (C3H/HeN) used as test animals are endotoxin-sensitive and, on the other hand, mice (C3H/HeJ) are endotoxin-insensitive.

As is apparent from the test results, Lipid A showed substantially no activity in C3H/HeJ, whereas GSL-2 showed a similar degree of activities in the two types of mice.

From the test results, it was Found that the mitogen activities of GSL-2 and endotoxin are Induced by different mechanisms.

2. Other Biological Activities

Biological activities and toxicity of the object substance (GSL-2) of the present invention were determined, and the results obtained are summarized in Table 2.

TABLE 2

| | |
|---|---|
| Lethal Toxicity | —a |
| Tolerance-inducing Ability | —a |
| TNF-inducing Activity | — |
| Limulus Activity | —b |

Note:
a; Galactosamine-sensitized C57BL/6 mice were used. In the tolerance-inducing test, LPS was injected after 3 hours.
b; Toxicolor system (produced by Seikagaku Kogyo K.K.) was used.

In the measurement of the lethal activity of the object substance, no activity was found at 10 μg per mouse. With respect to the tolerance-inducing ability against the lethal toxicity, no activity was found at a dose up to 50 μg per mouse. The TNF-inducing activity was measured at a dose up to 50 μg per mouse, but no induction ability was detected. Regarding the limulus activity, slight colorization was noted at a concentration of 10 μg/ml in the toxicolor system, but, as compared with Salmonella lipopolysaccharides, a sensitivity difference to a degree of more than $10^6$ times was observed.

Effect of the Invention

The novel compound which is isolated and identified according to the present invention exhibits a cell differentiation-inducing ability and can be used as an agent utilizing this activity. Also, the compound can be used as an activator of B cells.

I claim:

1. A glycosphingolipid represented by the following formula:

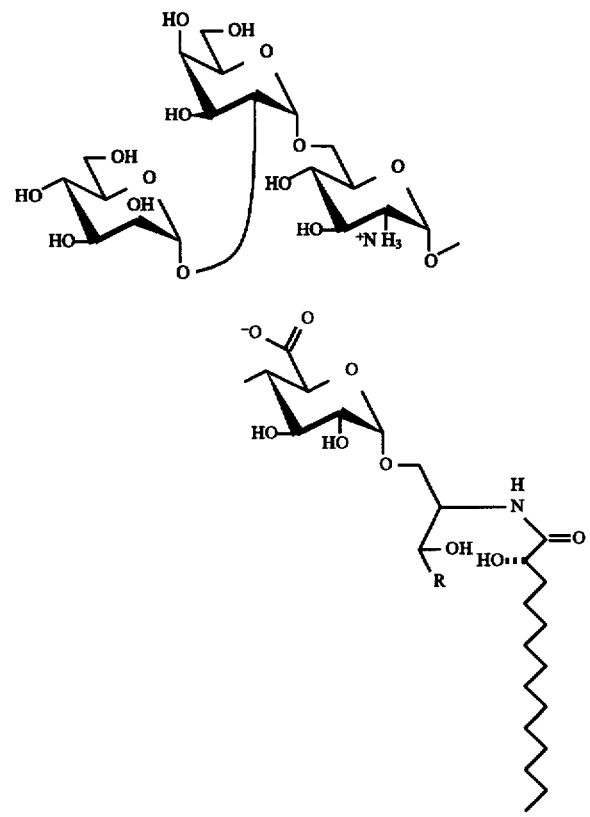

wherein R is:

2. A glycosphingolipid represented by the formula:
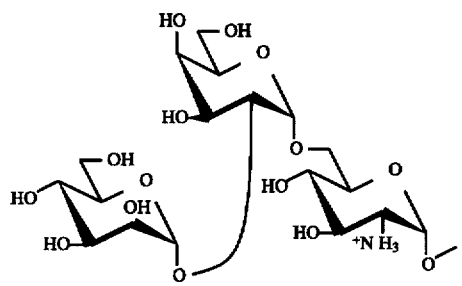
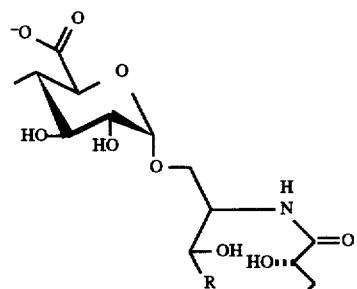
wherein R is:
* * * * *